United States Patent
Delfino et al.

(10) Patent No.: US 6,264,595 B1
(45) Date of Patent: Jul. 24, 2001

(54) RADIOACTIVE TRANSITION METAL STENTS

(75) Inventors: Michelangelo Delfino; Mary Elizabeth Day, both of Los Altos, CA (US)

(73) Assignee: Mobeta, Inc., Los Altos, CA (US)

( * ) Notice: Subject to any disclaimer, the term of this patent is extended or adjusted under 35 U.S.C. 154(b) by 0 days.

(21) Appl. No.: 09/244,348

(22) Filed: Feb. 4, 1999

(51) Int. Cl.[7] ........................................ A61N 5/00
(52) U.S. Cl. ...................................... 600/1; 600/3
(58) Field of Search ........................... 600/1, 2, 3

(56) References Cited

U.S. PATENT DOCUMENTS

| | | |
|---|---|---|
| 5,059,166 | 10/1991 | Fischell et al. . |
| 5,176,671 | 1/1993 | Fischell et al. . |
| 5,674,177 | * 10/1997 | Hehrlein et al. ........................ 600/3 |
| 5,722,984 | 3/1998 | Fischell et al. . |
| 5,800,507 | 9/1998 | Schwartz et al. . |
| 5,840,009 | 11/1998 | Fischell et al. . |
| 5,851,315 | 12/1998 | Strathearn et al. . |
| 5,919,126 | * 7/1999 | Armini ................................. 600/3 |

OTHER PUBLICATIONS

Carter et al., "Effects of Endovascular Radiation From a β–Particle–Emitting Stent in a Porcine Coronary Restenosis Model," *Circulation* 94(10):2364–2368 (1966).

Carter et al., "Experimental Results With Endovascular Irradiation Via A Radioactive Stent," *Int. J. Radiation Oncology Biol. Phys.* 36(4):797–803 (1996).

* cited by examiner

*Primary Examiner*—Max Hindenburg
*Assistant Examiner*—Brian Szmal
(74) *Attorney, Agent, or Firm*—Robins & Associate

(57) ABSTRACT

A radioactive transition metal stent, comprising one or more transition metals, wherein the transition metal stent surface is chemically bound to a radioactive material; and a method for producing the radioactive transition metal stent wherein the radioisotope is chemically bound to, and is uniformly confined to the transition metal stent surface without affecting the metallurgical properties of the transition metal stent is disclosed.

7 Claims, 2 Drawing Sheets

RADIOACTIVE TRANSITION METAL STENTS

TECHNICAL FIELD

This invention relates generally to intravascular implantation devices and more particularly to a radioactive transition metal stent, wherein the stent surface comprises chemically-bound radioisotope, for therapeutic and diagnostic applications.

BACKGROUND OF THE INVENTION

Intravascular stents have been permanently implanted in coronary or peripheral vessels to prevent restenosis. See, e.g. U.S. Pat. Nos. 5,800,507; 5,059,166 and 5,840,009. Trauma or injury to the artery caused by angioplasty procedures, implantation of stents, atherectomy or laser treatment of the artery, result in restenosis, i.e., the closure or renarrowing of the artery. Restenosis, a natural healing reaction to the injury of the arterial wall, begins with the clotting of blood at the site of the injury, followed by intimal hyperplasia, i.e. the rapid growth of the injured arterial tissue through the openings in the stent, and the migration and proliferation of medial smooth muscle cells, until the artery is again stenotic or occluded.

However, such stents are not always effective in preventing restenosis and can cause undesirable local thrombosis. A variety of solutions have been proposed to minimize these undesirable effects, such as coating the stents with a biocompatible or an anti-thrombotic surface, wherein the stent-surface is seeded with endothelial cells or fibrin, or using stents as drug delivery devices. See for example, U. S. Pat. Nos. 5,800,507;5,059,166; WO 91/12779 and WO 90/13332.

Implanted stents, in conjunction with endovascular irradiation, are believed to prevent restenosis by alleviating neointimal hyperplasia. The beta-particle emitter, phosphorus-32 ($^{32}$P) radioisotope, has been used as a permanent medical implant. Fischell et al. describe stents formed from radioactive materials, wherein a radioisotope is incorporated into the stent by physical methods, such as coating, plating, implanting on the exterior surface of the stent; inserting inside the stent; and alloying into the metal from which the stent is made. Alternatively, a beam of an ionized radioisotope is directed on the surface of the stent. See U.S. Pat. Nos. 5,059,166, 5,176,617, 5,722,984, and 5,840,009. Typically, an ion-implantation method requires irradiating sublimed red phosphorous (to avoid contamination) for about ten days to achieve a sufficient concentration of phosphorous-32 ($^{32}$P) to obtain radioactivity of 4 to 13 $\mu$Ci per stent. However, this method is expensive, requires sophisticated equipment, and the transfer of the radioactive source from the nuclear reactor to the ion-implanter to the medical site adversely affect the short half-life of phosphorous-32 ($^{32}$P) (14.3 days). Additionally, ion-implantation damages the surface of the stent, the interstitially implanted phosphorous-32 ($^{32}$P) diffuses rapidly and is relatively unstable compared to chemically bound phosphorous-32 ($^{32}$P). Moreover, ion-implantation requires beam and/or substrate scanning to achieve uniformity, which is difficult to obtain on a radial open-mesh stent. Thus conventional methods result in lower quality, non-uniform radioactive stents.

Strathearn, et al. describe a process for diffusing chemically bound radioactive ions below the surface of the substrate, wherein diffusion is accomplished by heating the substrate between 300° to 600° C. (U.S. Pat. No. 5,851,315). However, current techniques do not provide for radioactive stents with a radioisotope concentrated at the point of maximum tissue penetration, wherein the radioisotope, such as phosphorus-32 ($^{32}$P), is chemically bound to and is uniformly confined to the surface without affecting the metallurgical properties, such as ductility and malleability, of the stent. Thus, there is a need for improved and cost-effective radioactive stents, wherein the radioisotope is uniformly distributed over the surface and is concentrated at the point of maximum tissue penetration.

SUMMARY OF THE INVENTION

The present invention relates to a radioactive transition metal stent, comprising one or more transition metals, wherein the transition metal surface is chemically bound to a radioactive material; and a method of producing the radioactive transition metal stent wherein the radioisotope is chemically bound to and is uniformly confined to the transition metal surface without affecting the metallurgical properties of the stent. Unlike conventional methods, the present method does not rely on the complex techniques described above. Accordingly, the present invention provides an improved and cost-effective radioactive transition metal metaphosphate stent surface and a method of making the same.

In one aspect, the invention relates to a radioactive transition metal stent comprising one or more transition metals, wherein the transition metal surface is chemically bound to a radioactive material, and further wherein the transition metal is a single element or an alloy of two or more transition metals. In a preferred embodiment, the radioactive material comprises a phosphorus-32 ($^{32}$P) metaphosphate, wherein the radioactivity of the transition metal stent ranges from about 0.1 $\mu$Ci to about 100 $\mu$Ci per stent.

In another aspect, the invention relates to a method of producing a radioactive transition metal stent, comprising one or more transition metals wherein the transition metal surface is chemically bound to a radioactive material, comprising:

(i) providing a solution of dehydrated phosphorus-32 ($^{32}$P) enriched metaphosphoric acid;

(ii) mixing the phosphorus-32 ($^{32}$P) enriched metaphosphoric acid with a inert polymer to form an emulsion;

(iii) stabilizing the emulsion;

(iv) immersing a transition metal stent in the stabilized emulsion;

(v) removing the stent from the emulsion; and (vi) washing and drying the stent to obtain the radioactive transition metal metaphosphate stent.

In an alternative embodiment, the stent is further immersed in a suitable non-polar solvent with a low dielectric constant, such as n-hexane, chloroform, carbon tetrachloride, diethyl ether, and the like, to remove the residual polymer. In a preferred embodiment, the non-polar solvent is n-hexane.

In preferred embodiments, the transition metal is a single element or an alloy of two or more transition metals and the inert polymer is a polysiloxane polymer. In another preferred embodiment, the phosphorus-32 ($^{32}$P) enriched metaphosphoric acid has a radioactivity of about 1 mCi to about 10,000 mCi per ml and is mixed with a linear polysiloxane polymer to form an emulsion, wherein the emulsion is stabilized at a temperature between 150° C. to about 300° C., and further wherein the stent is immersed in the emulsion for a duration of between about 10 minutes to about 180 minutes to yield a transition metal stent metaphosphate having a radioactivity of about 0.1 $\mu$Ci to about 100 $\mu$Ci per stent.

In an alternative embodiment, the transtion-metal stent is microscopically roughened prior to immersion or concomitantly in the emulsion. In a preferred embodiment, the transtion-metal stent is microscopically roughened in the upper stent surface.

These and other embodiments of the present invention will readily occur to those of ordinary skill in the art in view of the disclosure herein.

DETAILED DESCRIPTION

Figure 1:
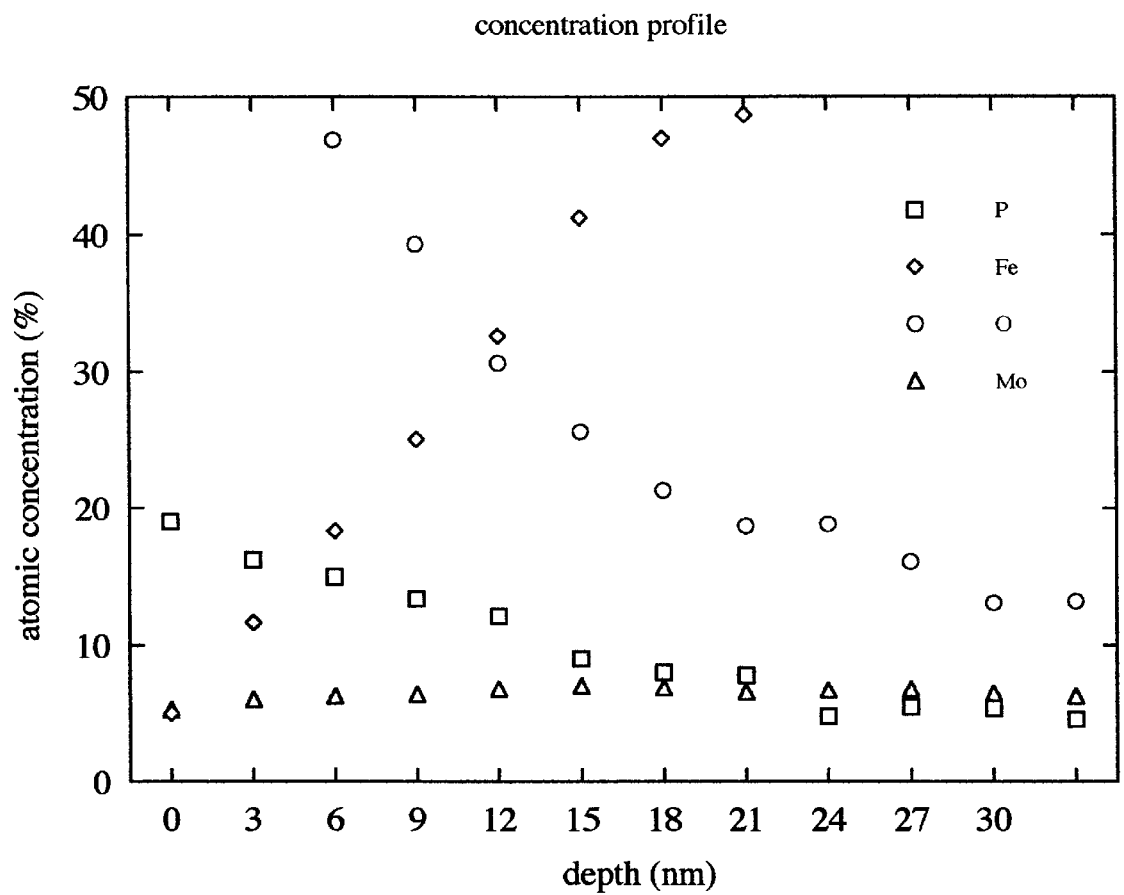
FIG. 1 illustrates the X-ray photoelectron spectroscopy (XPS) sputter depth profile for a radioactive stainless steel stent of the invention.

The practice of the present invention will employ, unless otherwise indicated, conventional techniques of chemistry, biochemistry, and medicine, including diagnostics, which are within the skill of the art. Such techniques are explained fully in the literature. See, e.g., *Principles of Physical Chemistry*, Maron, S. H. and Prutton, C. F., ($4^{th}$ Edition, 1965, The MacMillan Company) and *Advanced Inorganic Chemistry*, Cotton, F. A. and Wilkinson, G., ($3^{rd}$ Edition, 1972, Interscience Publishers).

All patents, patent applications, and publications mentioned herein, whether supra or infra, are hereby incorporated by reference in their entirety.

A. Definitions

In describing the present invention, the following terms will be employed, and are intended to be defined as indicated below.

It must be noted that, as used in this specification and the appended claims, the singular forms "a", "an", and "the" include plural referents unless the content clearly dictates otherwise. Thus, for example, reference to "a transition metal" includes two or more such metals, and the like.

Unless defined otherwise, all technical and scientific terms used herein have the same meaning as commonly understood by one of ordinary skill in the art to which the invention pertains. The following terms are intended to be defined as indicated below.

As used herein, the terms "transition metal" or "transition element" refers to any element in which the filling of the outermost shell to eight electrons within a periodic table is interrupted to bring the penultimate shell from 8 to 18 or 32 electrons. Transition elements include, without limitation, scandium, titanium, vanadium, chromium, manganese, iron, cobalt, nickel, copper, zinc, ytterbium, zirconium, niobium, molybdenum, silver, lanthanum, hafnium, tantalum, tungsten, rhenium, rare-earth elements, cerium, praseodymium, neodymium, promethium, samarium, europium, gadolinium, terbium, dysprosium, holmium, erbium, thulium, yttrium, lutetium, and rhodium.

As used herein, the term "alloy" refers to a mixture of two or more transition metals. Examples of alloys include, but are not limited to, stainless-steel type 316, stainless-steel type 316L, nitinol (a nickel-titanium alloy), elgiloy (a cobalt-nickel alloy), all commercially available from, e.g. Alan Steel & Supply Co., Redwood City, Calif.; Carpenter Technology Corp., Hayward, Calif.; Shape Memory Applications, Inc., Santa Clara, Calif. and Elgiloy Ltd. Partnership, Elgin, Ill.

As used herein, the term "stent" refers to a metallic surface, wherein the metal may be any geometrical shape or form, such as round, rectangular, square, cylindrical, flat surfaces, catheters, wires, helically coiled spring, and the like. In a preferred embodiment, the metal may be any material or device used to support a tissue, graft or anastomosis during the healing process. In another preferred embodiment, the stent is in the form of a cylindrical wire.

As used herein, an "inert polymer" refers to a liquid that does not react with the stent metal or the dehydrated phosphorus-32 enriched metaphosphoric acid, and does not cause the soluble phosphorus-32 concentration to be reduced. Examples of inert polymers include, but are not limited to, a linear polysiloxane polymer having a room-temperature kinematic viscosity of 0.1 to 1000 CS, high temperature oils and lubricants having a flash point below 250° C., preferably a flash point of between 190°–250° C., and more preferably between 200°–230° C.

As used herein, the term "kinematic viscosity" is defined as the ratios of viscosity coefficient divided by density. A standard kinematic viscosity unit is a CS.

B. General Methods

Before describing the present invention in detail, it is to be understood that this invention is not limited to particular transition metal stents or process parameters as such may, of course, vary. It is also to be understood that the terminology and examples used herein are for the purpose of describing particular embodiments of the invention only, and are not intended to be limiting.

Although a number of transition metal stents and methods similar or equivalent to those described herein can be used in the practice of the present invention, the preferred materials and methods are described.

The invention provides a radioactive transition metal stent and a method of producing the same. Stents for use with the present invention can be of any useful geometrical shape or form, as described above. Generally, stents have a radial area that may be approximated as half that of a cylindrical tube. Thus the surface area of a typical 0.3 cm diameter, 2 cm long stent is approximately 2 cm$^2$. The length of the stent will vary depending on the particular application and can be as long as 45 mm and as short as 1.5 mm.

Using currently available techniques, a radioactive doped transition metal metaphosphate stent may be produced as follows. For example, for a 10 nm thick transition metal metaphosphate containing 20% phosphorous, e.g., Me$_2$(PO$_3$)$_3$, having a typical density of 5×10$^{22}$ atoms/cm$^3$, there are a total of 1×10$^{16}$ phosphorus atoms/cm$^2$. A transition metal metaphosphate grown uniformly on a 2 cm stent as described above, would accommodate 2×10$^{16}$ phosphorus atoms. The radioactive phosphorus atoms must be present in a concentration sufficient to permit efficient transfer of radioactive atoms from an appropriate chemical source to the stent. For example, the ratio of available phosphorus in 0.5 ml anhydrous orthophosphoric acid (H$_3$PO$_4$) to that to be incorporated into the stent is approximately 300,000:1. Thus, 1.0 Ci phosphorus-32 enriched acid will yield a 3.3 $\mu$Ci phosphorus-32 enriched stent.

Uniform and continuous contact with the stent using such a small volume of the very viscous orthophosphoric acid is impractical and not feasible. Thus to obtain a radioactive transition metal stent, wherein the radioisotope is chemically bound to, and is uniformly confined to the transition metal surface without affecting the metallurgical properties of the stent, it is necessary to increase the effective contact area of the stent surface with the orthophosphoric acid, without degrading or reducing the radioactive concentration of the acid. The instant invention provides a method wherein the transition metal stent is in uniform and continuous contact with the radioactive metaphosphoric acid. The radioactively enriched acid is suspended in a suitable emulsion, and the transition metal stent is then immersed in the stabilized emulsion to allow a uniform, surface-controlled metaphosphate growth on the transition metal stent surface. Additionally, more than one radioactive stent can be produced simultaneously using the method of the invention, thus adding to the cost-effectiveness of the radioactive stents.

A procedure for producing a radioactive transition metal stent in which the radioisotope is chemically bonded to the transition metal stent surface is described as follows. In preferred embodiments, the transition metal is a single element or an alloy of two or more transition metals and the inert polymer is a polysiloxane polymer.

Metaphosphoric acid ($HPO_3$), (wherein n=3 or 4) is prepared according to known procedures. (See The Merck Index, $9^{th}$ Ed, 1976, page 956). Phosphorus-32 enriched 85% $H_3PO_4$ is heated in an open vessel at a temperature above 300° C., preferably about 300° C. to about 420° C., and most preferably about 310° C. to about 350° C.; for approximately about 5 to 50 hours, preferably 20 to 50 hours, and most preferably 20 to 30 hours, to yield the metaphosphoric acid having a radioactivity of about 1 mCi to about 10,000 mCi per ml, preferably 10 mCi to about 7,000 mCi per ml, and more preferably 100 mCi to about 3,000 mCi per ml. An inert polymer is added to the metaphosphoric acid to form an emulsion, wherein the volume ratio of acid to polymer ranges from about 1:1 to about 1:500, preferably from about 1:1 to about 1:300, and most preferably from about 1:2 to about 1:10. The emulsion is then stabilized, i.e. equilibrated, with agitation, at about 150–300° C. A transition metal stent having a thickness of about 10 nm to about 1000 nm, preferably about 10 nm to about 700 nm, and more preferably about 10 nm to about 500 nm, is completely immersed in the emulsion for about 10–120 minutes, preferably 10 to 180 minutes, and most preferably 30 to 60 minutes, while being gently agitated so that it is in constant contact with the acid globules. The stent is then removed from the emulsion, rinsed in boiling deionized water, rinsed again in room temperature deionized water, and dried using nitrogen gas. The stent is then optionally immersed in a suitable non-polar solvent with a low dielectric constant, such as n-hexane, chloroform, carbon tetrachloride, diethyl ether, and the like, to remove the residual polymer.

The radioactivity of the stent is measured using a suitable beta-particle counter and readied for permanent or temporary endovascular implantation, such as cornary, iliac, urethral, biliary stents, and the like. In an alternative embodiment, the radioactive stent may additionally comprise antithrombogenic agents. In one embodiment, the radioactive stent is temporarily placed within the lumen of a vessel, for example a thin wire with a radioactive tip is placed within the bile duct, wherein the wire can be withdrawn after a limited time.

In preferred embodiments, the transition metal stent has a radioactivity of about 0.1 $\mu$Ci to about 100 $\mu$Ci, preferably of about 0.2 $\mu$Ci to about 90 $\mu$Ci, and more preferably of about 0.5 $\mu$Ci to about 80 $\mu$Ci per stent; wherein about 1% to about 67%, preferably about, and more preferably about 1% to about 33% of the total surface comprises chemically bound phosphorus-31 and phosphorus-32 atoms. The chemically-bound phosphorous-32 is incorporated primarily on the surface of the stent, up to a depth of about 300A°, preferably about 200A°, most preferably 100A° from the surface of the stent.

In another embodiment, the transtion metal stent is microscopically roughened, using known procedures, prior to immersion in the emulsion. In an alternative embodiment, the transtion metal stent is microscopically roughened during immersion in the emulsion In a preferred embodiment, the transtion-metal stent is microscopically roughened in the upper stent surface. For example, the transition metal stent may be roughened by chemically etching the stent either prior to being placed in the emulsion, or the stent may be etched during immersion by the acidic emulsion. Generally, etching with chemicals, such as acid solutions, e.g., HCI solution, causes the surface to pit and roughen.

The following examples are illustrative in nature, and are not intended to limit the scope of the present invention in any manner.

EXAMPLE 1

Metaphosphoric acid $(HPO_3)_n$ (wherein n=3 or 4) is prepared according to known procedures. (See The Merck Index, $9^{th}$ Ed, 1976, page 956). Phosphorus-32 enriched 85% $H_3PO_4$ (0.5 ml) is heated in an open vessel at a temperature above 300° C. for approximately about 5 to 50 hours to yield the metaphosphoric acid having a radioactivity of about 1 mCi to about 10,000 mCi per ml. Dimethylpolysiloxane polymer (Dow Corning, boiling point >200° C. and a kinematic viscosity of about 20 CS) (20 ml) is added to the metaphosphoric acid to form an emulsion. The emulsion is then stabilized, with agitation, at about 150–200° C. A stent, such as a stainless steel type 316L stent is completely immersed in the emulsion for about 10–120 minutes, while being gently agitated so that it is in constant contact with the acid globules. The stent is then removed from the emulsion, rinsed in boiling deionized water, rinsed again in room temperature deionized water, and dried using nitrogen gas. The stent is then optionally immersed in a suitable non-polar solvent with a low dielectric constant, such as n-hexane, chloroform, carbon tetrachloride, diethyl ether, and the like, to remove the residual polymer.

EXAMPLE 2

Radioactive stainless steel type 316 stents (1.9 $cm^2$) (Alan Steel & Supply Co., Redwood City, Calif.) were produced according to the procedure described in Example 1 above.

Metaphosphoric acid was prepared as follows. Orthophosphoric acid (4.5 ml) was added to a vitreous carbon crucible (3.2 cm diameter, 4.6 cm deep) housed in a temperature controlled copper block heater. A chromel-alumel thermocouple inserted in the copper block was used to monitor the temperature and as a feedback loop for controlling temperature. The copper block was incrementally heated over a period of 45 minutes as follows: the temperature was raised to 153° C. in 10 minutes; to 175° C. in 20 minutes; to 200° C. in 30 minutes; to 210° C. in 36 minutes and finally to 330° C. in 45 minutes. The copper block was maintained at 330° C. for 19 hours, to yield the metaphosphoric acid.

The temperature of the copper block was lowered to 215° C. in 10 minutes. Dimethoxypolysiloxane polymer (Dow Corning 220 fluid, 20 CS kinematic viscosity) (4.9 ml) was then added to the crucible containing the metaphosphoric acid and the emulsion was stabilized at 215° C. The stainless steel type 316 stent was placed in the crucible and stirred periodically for 30 minutes. The stent was removed from the emulsion and placed in a pyrex beaker containing tap water (room temperature). The stent was then rinsed under running tap water and dried. The stent was subsequently dipped in n-hexane to remove any residual polymer.

FIG. 1 illustrates the X-ray photoelectron spectroscopy (XPS) sputter depth profile for a radioactive stainless steel stent, wherein the atomic concentration (%) is plotted against the depth (nm) for the elements, P, Fe, O and Mo. The radioactive stent contains about 20% chemically-bound phosphorous, incorporated primarily on the surface of the stent, up to a depth of approximately 20 nm.

Figure 2:
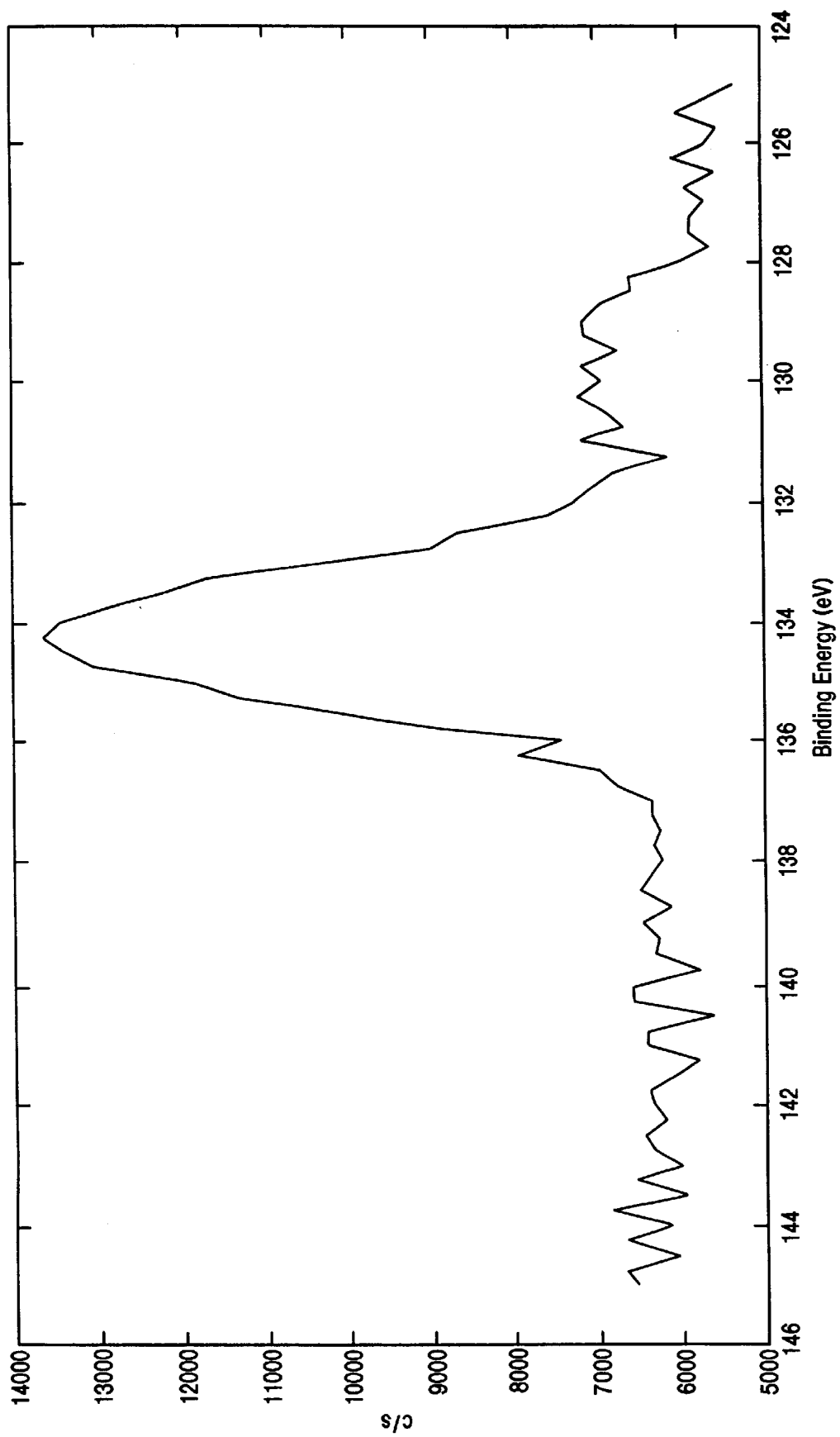
FIG. 2 illustrates the binding energy profile for a radioactive stainless steel stent of the invention.

FIG. 2 illustrates the binding energy (eV) for the phosphorous $2p^{3/2}$ core-level transition measured according to standard procedures. As evidenced from FIG. 2, all of the phosphorous is chemically bound: the peak at 134 eV corresponds to the metaphosphate and the peak at 130 eV corresponds to reduced phosphorous, i.e. phosphide.

Thus, a radioactive transition metal stent, comprising one or more transition metals, wherein the transition metal stent surface is chemically bound to a radioactive material is disclosed. A method for producing the radioactive transition metal stent wherein the radioisotope is chemically bound to, and uniformly confined to the stent surface without affecting the metallurgical properties of the stent is also disclosed. Although preferred embodiments of the invention have been described in some detail, it is understood that obvious variations can be made without departing from the spirit and scope of the invention as defined by the appended claims.

What is claimed is:

1. A radioactive transition metal stent, comprising one or more transition metals, wherein the transition metal stent surface is chemically bound to a radioactive material, and further wherein the radioactive material comprises a metaphosphate or a phosphide surface.

2. The radioactive transition metal stent of claim 1 wherein the transition metal is a single element or an alloy of two or more transition metals.

3. The radioactive transition metal stent of claim 2, wherein the transition metals are selected from a group consisting of scandium, titanium, vanadium, chromium, manganese, iron, cobalt, nickel, copper, zinc, ytterbium, zirconium, niobium, molybdenum, silver, lanthanum, hafnium, tantalum, tungsten, rhenium, rare-earth elements, cerium, praseodymium, neodymium, promethium, samarium, europium, gadolinium, terbium, dysprosium, holmium, erbium, thulium, yttrium, lutetium and rhodium.

4. The radioactive transition metal stent of claim 2, wherein the transition metal is an alloy selected from a group consisting of stainless-steel type 316, stainless-steel type 316L, a nickel-titanium alloy and a cobalt-nickel alloy.

5. The radioactive transition metal stent of claim 1 wherein the radioactive material comprises a metaphosphate surface wherein about 1% to about 67% of the total surface comprises chemically bound phosphorus-31 and phosphorus-32 atoms.

6. The radioactive transition metal stent of claim 5, wherein the metaphosphate surface comprises a radioactivity of about 0.1 $\mu$Ci to about 100 $\mu$Ci per stent.

7. The radioactive transition metal stent of claim 5 wherein said chemically-bound phosphorus-32 has a depth of about 300 A° to about 100 A° from the surface of the stent.

* * * * *